United States Patent [19]

Nelson

[11] 4,170,230
[45] Oct. 9, 1979

[54] BREATHING APPARATUS

[76] Inventor: Byron G. Nelson, P.O. Box 6457, Lake Charles, La. 70606

[21] Appl. No.: 896,303

[22] Filed: Apr. 14, 1978

[51] Int. Cl.² ............................................. A61M 15/00
[52] U.S. Cl. ..................................... 128/139; 128/136
[58] Field of Search ........... 128/139, 136, 137, 132 R, 128/140 R, 147, 208, 222, 239; 32/33

[56] References Cited

U.S. PATENT DOCUMENTS

| 587,358 | 8/1897 | Anderson | 128/136 |
| 4,071,026 | 1/1978 | Bevins | 128/136 X |

FOREIGN PATENT DOCUMENTS

| 444852 | 8/1924 | Fed. Rep. of Germany | 32/33 |
| 1248474 | 10/1971 | United Kingdom | 128/136 |

*Primary Examiner*—Henry J. Recla
*Attorney, Agent, or Firm*—Edgar E. Spielman, Jr.; David L. Ray

[57] ABSTRACT

A breathing apparatus is disclosed which fits into the mouth of a human between the teeth and cheeks. The apparatus functions to direct air from the front of the mouth to the back of the mouth and from there to the lungs. The apparatus features a ported curved tube which is open-ended and which has sufficient length to extend from the rear of the mouth on one side of the mouth along a path following the tooth line from one set of molars to the other and on to the rear of the mouth on that other side of the mouth. To facilitate flow of air from the front of the mouth to the rear, there is provided an intake opening located midway the tube so that said opening will be in a position at the front of the mouth. Exhaust openings are provided in conjunction with each open end of the apparatus for allowing passage of the air from the tube into the rear of the mouth and upper trachea. The intake and exhaust openings together with the cross-sectional area of the curved tube are designed so that when the user is breathing through the apparatus, the flow of air therefrom will be approximate to that flow of air as could be expected with normal nasal breathing.

9 Claims, 8 Drawing Figures

BREATHING APPARATUS

BACKGROUND OF THE INVENTION

There are many people who are bothered with a nasal blockage which hinders their breathing, especially at night when they are attempting to sleep. A nasal blockage can either be in one or both nostrils, but in either case the sufferer usually ends up breathing through his or her mouth. Mouth breathing is recognized as being unhealthy as it contributes not only to an unpleasant dry mouth syndrome, but also contributes to the development of gum diseases such as pyorrhea.

It is therefore an object of this invention to provide a breathing apparatus which the user can wear inside of the mouth between the cheeks and teeth to allow the user to breathe through his or her mouth without drying out the mouth or causing gum disease problems. While accomplishing these advantages, the apparatus of this invention allows for freedom of tongue, lip and jaw movement, these movements being essential in effecting comfortable respiration and in effecting the salivation adjusting function of swallowing.

THE INVENTION

This invention relates to a breathing apparatus fitable into the mouth of a human between the cheeks and teeth which apparatus includes: a curved tube being open-ended and having sufficient length to extend along a path following the tooth line from a point adjacent one set of molars to a point adjacent the other set of molars; at least one intake opening located midway the tube so that said opening will be positioned toward the outside of the mouth and proximate to the middle of the mouth; and at least one exhaust opening on each side of the curved tube facing the inside of the mouth, proximate the open ends of the tube and located at a point above the lower-most point of the tube. The intake opening and the exhaust openings are sized in combination with the cross-sectional area of the tube to provide a flow of air through the curved tube approximate the flow of air that the human could achieve through normal nasal breathing.

As can be seen from the above, the apparatus of this invention, when in the human mouth will direct air from the front of the mouth between open lips to the rear portion of the mouth and on down to the trachea. By routing the air to the rear of the mouth, the user of this invention avoids exposing much of his or her mouth to the drying and deleterious effects of an otherwise uncontained air passage over and through the several parts of the mouth.

Another embodiment of this invention features a breathing apparatus which may be used by a person suffering from a less severe nasal blockage. This embodiment includes a tube portion and a curved seal portion with the tube portion having a front open end and a rear open end to include the lateral exhaust opening. The curved seal portion extends from the front open end across the remaining front of the mouth to effect a seal so that the air is prevented from passing through the mouth except through the tube portion of the apparatus. Near the back of the tube portion there is located at least one exhaust opening which passes the air from the tube to the rear of the mouth and upper trachea.

These and other features of this invention contributing satisfaction in use and economy in manufacture will be more fully understood when taken in connection with the following description and illustrations in which identical numerals refer to identical parts and in which.

Figure 1:
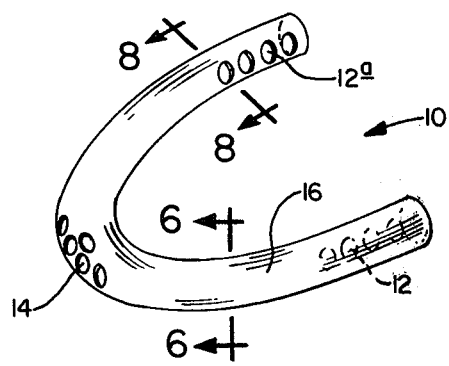
FIG. 1 is a perspective view of one embodiment of this invention.

Referring now to the embodiment shown in FIGS. 1 and 4–8, it can be seen that the breathing apparatus of this invention, generally designated by the numeral 10, includes an open-ended curved tube 16. The drawings show open-ended curved tube 16 in a horseshoe shape. It is to be understood, however, that open-ended curved tube 16 may be a tube which is bent into a shape which is comfortable in the user's mouth and thus provide some degree of a custom fit. Open-ended curved tube 16 may be constructed of any materials which are inert in the human mouth. Such materials are well-known to those skilled in the art. For example, latex rubber has received wide acceptance for oral use. Plastics which are presently used in the medical field which have the aforedescribed characteristics are also quite satisfactory. The desirability of soft, flexible materials of construction for open-ended curved tube 16 is to be understood; however, open-ended curved tube 16 may be of a rigid material should the particular circumstance require such rigidity.

The cross-section shape of open-ended curved tube 16 in a direction transverse the long axis of curved tube 16 may be irregular or symmetrical as desired. For example, open-ended curved tube 16 may be elliptical in cross-section, circular in cross-section, or even rectangular in cross-section, or any combination thereof. It has been found through experience that open-ended curved tube 16, for achieving the greatest degree of comfort for the user of breathing apparatus 10, is preferably elliptical in cross-section since the lateral areas of the molars and gums of the upper and lower human jaws against which the apparatus will rest dictates a somewhat elliptical geometry.

The length of open-ended curved tube 16 should be that which is sufficient to extend from the rear of the mouth adjacent the right set of upper and lower molars, along the tooth pathway to a position to the rear of the other side of the mouth adjacent the left set of upper and lower molars. Since there is much variation in this length in the human population, construction of breathing apparatus 10 can be such that there may be a plurality of exhaust openings 12 and 12a. When there are a plurality of exhaust openings 12 and 12a the user can trim the length of open-ended curved tube 16 and still have a sufficient exhaust opening area available for suitable air flow. Apparatus 10, therefore, can be custom fitted as the user can determine for his or herself the length which he or she wishes apparatus 10 to be. In fact, apparatus 10 is capable of being shorter on one side than on the other to fit those people having irregular mouth shape.

The figures show that open-ended curved tube 16 has intake openings 14 which are located midway the tube so that when the tube is placed inside the user's mouth, these openings will be approximately centered in the mouth and facing towards the outside of the mouth. As shown in the drawing, there is a plurality of circular-shaped intake openings, however it is to be understood that so long as the total cross-sectional area of the intake openings allows for sufficient air flow, the intake openings may be of any shape in keeping with sound construction principles—for example, a slit or a plurality of slits may be used. Also, it is permissible and in some cases desirable to use a singular intake opening instead of the plurality shown in the drawings.

Figure 8:
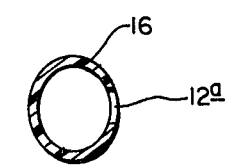
FIG. 8 is a sectional view taken through section lines 8—8 in FIG. 1.
Figure 7:
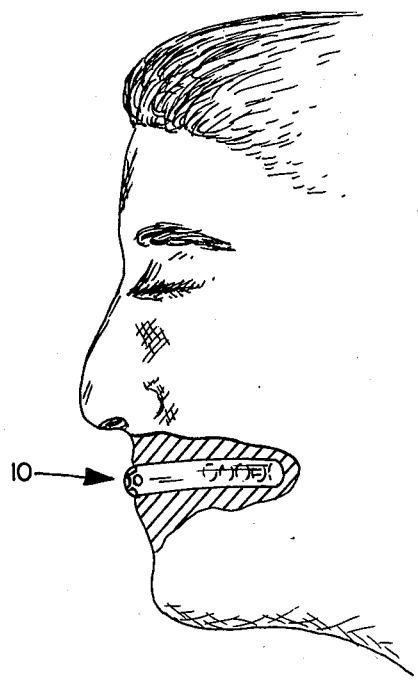
FIG. 7 is a view of the apparatus shown in FIG. 1 in place in a human's mouth.

Exhaust opening 12 and 12a are positioned facing towards the inside of the mouth at a point about midway the diameter of open-ended curved tube 16. These openings are positioned at a point above the lower-most point of open-ended tube 16 so that there will be available, beneath each opening, a channel for accumulated liquid to pass without the liquid passing through exhaust openings 12 or 12a. As is the case with intake openings 14, exhaust openings 12 and 12a may be of any convenient shape, size or number. A plurality of circular-shaped appertures for exhaust openings 12 and 12a has been found preferable for reasons of strength of construction and facility of fit. Alternatively, for example, exhaust openings 12 and 12a may consist of a slot or a plurality of slots in place of the circular appertures. The position of exhaust openings 12 and 12a to allow for proper drainage of the apparatus is shown in FIG. 8.

Figure 2:
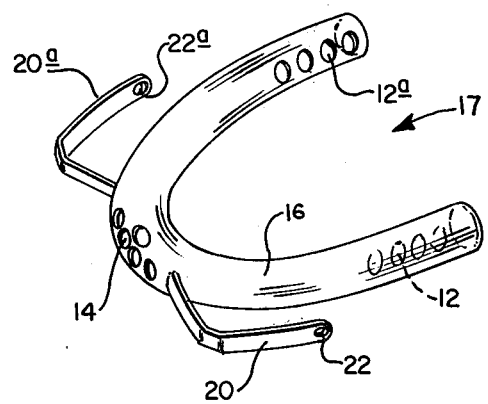
FIG. 2 is a perspective view of a second embodiment of this invention.
Figure 4:
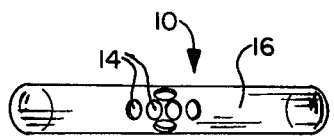
FIG. 4 is a front elevational view of the embodiment shown in FIG. 1.

Since the apparatus of this invention will be of most use when the user is in a reclined position sleeping, it will sometimes be desirable to provide means for insuring that the apparatus is maintained in proper position. In FIG. 2, another embodiment of this invention, generally designated by the numeral 17, is shown which provides for such maintenance. The embodiment shown in FIG. 2 is identical to the one shown in FIG. 1 except that the former has holding arms 20 and 20a. Those parts which are identical are identified with identical numbers and the description of these parts for the embodiment of FIG. 1 is equally applicable to this embodiment shown in FIG. 2.

Holding arms 20 and 20a are connected to open-ended curved tube 16 at a point adjacent the intake opening. These arms project outwardly and are spaced apart from open-ended curved tube 16 so that they will be positioned outside of the user's cheeks. In each end of holding arms 20 and 20a there is provided eyelets 22 and 22a respectively. To these eyelets there may be attached a holding band which will go around the user's head or neck as comfort dictates. By having the band around the head or neck, it can be appreciated that breathing apparatus 17 will be prevented from ejection from the user's mouth.

Figure 3:
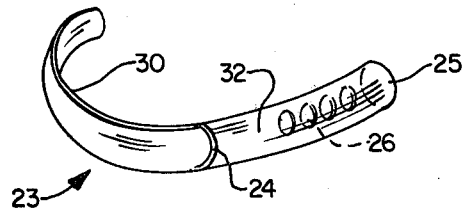
FIG. 3 is a perspective view of a third embodiment of this invention.
Figure 5:
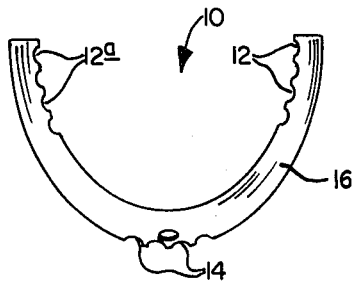
FIG. 5 is a top plan view of the embodiment shown in FIG. 1.
Figure 6:
FIG. 6 is a sectional view taken through section lines 6—6 in FIG. 1.

In FIG. 3 there is shown yet a third embodiment of this invention. This embodiment will be especially useful to those who only suffer from partial nasal blockage. For these people the apparatus shown in FIG. 3 and generally designated by the numeral 23, will be worn in the mouth on the side of the mouth most suited to them for comfortable breathing. As can be seen, apparatus 23 has a tube portion 32 and a curved sealing portion 30. Curved sealing portion 30 is of a length and shape to insure that it fits across the user's teeth to form a seal so that air will not pass through the user's mouth, but rather will only pass through tube portion 32.

Tube portion 32 has a front open end 24 and a back open end 25. Adjacent to back open end 25 there is provided exhaust openings 26. Tube portion 32 is of a length to insure that air passing therethrough will exit said tube portion approximate the molars at the rear of the user's mouth. Exhaust openings 26 are of the type described above in the discussion of exhaust openings 12 and 12a and the description of these exhaust openings is equally applicable to exhaust openings 26.

Like the embodiments shown in FIGS. 1 and 2, it is possible to partially close off the rearmost open end of tube portion 32 as the need for strength requires, keeping in mind that the closed off portion is preferably on the upper edge of the tube so that proper draining of the tube can occur.

It can be appreciated from the foregoing that the abovedescribed embodiments of this invention provide the user with a means for comfortably breathing through his or her mouth. Due to variability of the tube length it is possible to have the tube extend to the rearmost portion of the user's mouth or to a point along the molar line. Thus, the relatively dry air which is inhaled is routed around the saliva glands and gums and thus does not become an irritant thereto; the saliva which would otherwise be evaporated by an uncontained air flow will, as a result of the use of this apparatus, remain available for lubricating the separate parts of the mouth and tongue as well as the laryngeal area of the trachea. To minimize gum irritation the further to the rear of the mouth which the tube extends the better the results.

Not only is there a positive effect from utilizing the apparatus of this invention, the apparatus is also comfortable to wear as it allows for free movement of lips, tongue and jaws, the free movement thereby effecting an ease in the salivation adjusting function of swallowing.

The apparatus of this invention can be made by conventional means such as by injection molding, extrusion, etc.

What is claimed:

1. A breathing apparatus fitable into the mouth of a human between cheeks and teeth which apparatus includes:
   a. flexible curved tube means being open-ended and having sufficient length to extend along a path following the tooth line from a point adjacent one set of molars to a point adjacent the other set of molars;
   b. at least one intake opening located midway said curved tube means so that said intake opening will be positioned towards the outside of the mouth and proximate to the middle of said mouth; and,
   (c) at least one exhaust opening in each side of said curved tube means adapted to face the inside of said mouth, proximate the open ends of said curved tube and located at a point above the lower-most point of said curved tube means, said intake and said exhaust openings being, in combination with the cross-sectional area of said curved tube means, a size sufficient to allow a flow of air through said curved tube approximate to the flow of air that said human could achieve through normal nasal breathing.

2. The apparatus of claim 1 wherein said curved tube means is constructed of flexible material.

3. The apparatus of claim 1 wherein said exhaust opening is located midway the vertical width of said tube means.

4. The apparatus of claim 1 wherein said curved tube means is, in cross-section, taken transverse the long axis of said tube means, elliptically shaped.

5. The apparatus of claim 1 wherein there is additionally provided at a point proximate said intake opening, a pair of outwardly extending holding arms which fit on the outside of said cheeks when said apparatus is in position, said holding arms having eyelets therein for attachment of a band thereto for fitment around the head or neck of said human.

6. A breathing apparatus fitable in the mouth of a human between the cheek and teeth, which apparatus includes:
 a. tube means having a front open end and a back open end and having sufficient length to extend from the front of said mouth back down the side of said mouth adjacent the molars on that side of said mouth;
 b. curved sealing means adapted to extend from said front open end around the front of said mouth to an extent to seal off passage of air through said air front of said mouth except into said front open end; and,
 c. at least one exhaust opening facing to the inside of said mouth, proximate said back open end and located at a point above the lower-most point of said tube means; wherein said exhaust opening is of sufficient size to supply a flow of air approximate to the flow of air said human could achieve through normal nasal breathing.

7. The apparatus of claim 6 wherein said tube means is constructed of flexible material.

8. The apparatus of claim 6 wherein said exhaust opening is located at a point midway the vertical width of said tube means.

9. The apparatus of claim 6 wherein said tube means, in cross-section taken transverse the long axis of said tube means, is elliptically shaped.

* * * * *